United States Patent [19]

Miyake et al.

[11] Patent Number: 5,492,909
[45] Date of Patent: Feb. 20, 1996

[54] TRIAZOLOPYRIDAZINE DERIVATIVES, THEIR PRODUCTION AND USE

[75] Inventors: Akio Miyake, Hirakata; Masahiro Kajino, Toyonaka; Yasuko Ashida, Takatsuki, all of Japan

[73] Assignee: Takeda Chemical Industries, Ltd., Osaka, Japan

[21] Appl. No.: 225,981

[22] Filed: Apr. 12, 1994

[30] Foreign Application Priority Data

Apr. 12, 1993 [JP] Japan .................. 5-110042

[51] Int. Cl.⁶ .................. A61K 31/50; A61K 31/535; C07D 487/04; C07D 487/14
[52] U.S. Cl. .................. 514/233.2; 514/248; 544/115; 544/118; 544/234; 544/236; 564/95
[58] Field of Search .................. 544/236, 115, 544/118; 514/248, 233.2

[56] References Cited

U.S. PATENT DOCUMENTS

| | | | |
|---|---|---|---|
| 3,915,968 | 10/1975 | Bellasio et al. | 544/118 |
| 4,136,182 | 1/1979 | Lewis et al. | 514/233.2 |
| 5,145,850 | 9/1992 | Miyake et al. | 544/236 |
| 5,155,108 | 10/1992 | Miyake et al. | 544/236 |
| 5,202,324 | 4/1993 | Miyake et al. | 544/236 |

FOREIGN PATENT DOCUMENTS

| | | |
|---|---|---|
| 0248413 | 12/1987 | European Pat. Off. . |
| 0381132 | 8/1990 | European Pat. Off. . |
| 0440119 | 8/1991 | European Pat. Off. . |
| 0441339 | 8/1991 | European Pat. Off. . |
| 0444549 | 9/1991 | European Pat. Off. . |
| 0548923 | 6/1993 | European Pat. Off. . |
| 0562440 | 9/1993 | European Pat. Off. . |
| 0562439 | 9/1993 | European Pat. Off. . |

*Primary Examiner*—Emily Bernhardt
*Attorney, Agent, or Firm*—Foley & Lardner

[57] ABSTRACT

A compound of the formula:

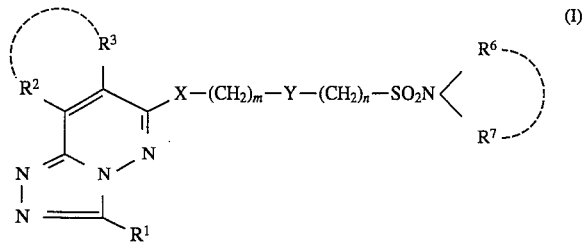

wherein $R^1$ is a hydrogen atom, a lower alkyl group or a halogen atom; $R^2$ and $R^3$ are a hydrogen atom, a lower alkyl group or a 5- to 7-membered cyclic group formed together with the adjacent —C=C—; X is an oxygen atom, a sulfur atom or a methylene group; Y is an optionally substituted methylene group, a divalent 3- to 7-membered homo- or heterocyclic group; $R^6$ and $R^7$ are a hydrogen atom, a lower alkyl group, a cycloalkyl group, an aryl group, or a nitrogen-containing heterocyclic group formed together With the adjacent nitrogen atom; m is an integer of 0 to 4; and n is an integer of 0 to 4, or a salt thereof. Said compound has an excellent anti-PAF activity, antiallergic action, etc., thus is useful as an antiasthmatic agent.

16 Claims, No Drawings

TRIAZOLOPYRIDAZINE DERIVATIVES, THEIR PRODUCTION AND USE

FIELD OF THE INVENTION

This invention relates to novel triazolopyridazine derivatives, their intermediate products, production of the derivatives and pharmaceutical preparations containing the derivatives. The triazolopyridazine derivatives of the present invention have excellent antiallergic, anti-inflammatory and anti-platelet activating factor (hereinafter referred to as PAF) actions, and are useful as, for example, antiasthmatics by controlling or inhibiting bronchospasm and bronchoconstriction.

BACKGROUND OF THE INVENTION

As an effective agent for a variety of diseases, various triazolopyridazine compounds have been studied. For example, U.S. Pat. No. 3,915,968 corresponding to Japanese Patent Publication No. 7439/1978 discloses a compound of the following formula:

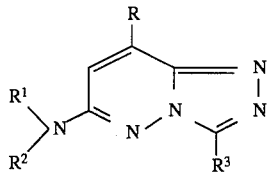

wherein R and $R^3$ respectively represent a hydrogen atom or a lower alkyl group (at least one of R and $R^3$ is a lower alkyl group), $R^1$ and $R^2$, taken together with the nitrogen atom, represent a heterocyclic ring selected from pyrrolidine, piperidine, piperazine and morpholine, or a salt thereof.

U.S. Pat. No. 4,136,182 discloses a compound shown by the following formula:

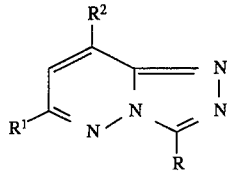

wherein R represents a hydrogen atom, phenyl, a lower alkyl or a lower alkyl carbonylamino; $R^1$ represents morpholino or piperidino; and $R^2$ represents a hydrogen atom or a lower alkyl, with the proviso that at least one of R and $R^2$ is a group other than hydrogen atom and with the further proviso that when R is phenyl, $R^1$ is morpholino and $R^2$ is a lower alkyl, or a salt thereof.

EP-A-248413 corresponding to Japanese Patent Application Laid-open No. 292784/1987 discloses a compound shown by the following formula:

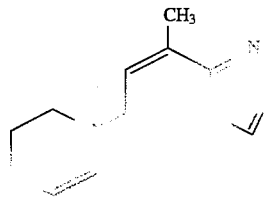

or a salt thereof.

These literatures disclose that the compounds mentioned above are useful as bronchodilators which alleviate bronchospasm.

Although a variety of antiasthmatics have been launched into markets, no antiasthmatic satisfactory in effects, continuity of action, safety or other factors has been developed. Therefore, the development of a novel compound having more effective antiallergic, antiinflammatory and anti-PAF actions, and having excellent properties for an antiasthmatic agent such as action sustainability, safety and the like has been desired.

SUMMARY OF THE INVENTION

Accordingly, it is an object of the present invention to provide novel compounds and salts thereof having more effective antiallergic, anti-inflammatory and anti-PAF actions.

It is another object of the present invention to provide novel compounds and salts thereof having excellent properties for antiasthmatic agents such as action sustainability and safety, thus being useful as antiasthmatic agents.

It is yet another object of the invention to provide methods of producing the novel compounds or salts thereof useful as antiasthmatic agents.

A still further object of the present invention is to provide intermediate products useful for producing such compounds or salts thereof.

A yet further object of the invention is to provide pharmaceutical compositions for antiasthmatic agents.

Another object of the present invention is to provide anti-PAF agents.

The invention also discloses methods of treating a disease caused by PAF activity, methods for inhibiting bronchoconstriction and uses of the triazolopyridazine derivatives or salts thereof as anti-PAF agents or antiasthmatic agents.

As a result of extensive studies on chemical modification of triazolopyridazine derivatives, the present inventors found that the compounds having a [1,2,4]triazolo[4,3-b] pyridazine skeleton which is novel and quite different in chemical structure from the known compounds have unexpectedly excellent antiallergic, antiinflammatory and anti-PAF actions, and excellent properties such as action sustainability and safety. Said compounds have been also found to control or inhibit bronchospasm and bronchoconstriction, thus being useful as antiasthmatic agents. The present invention has been accomplished based on these findings.

Thus, the present invention provides a compound shown by the following general formula (I):

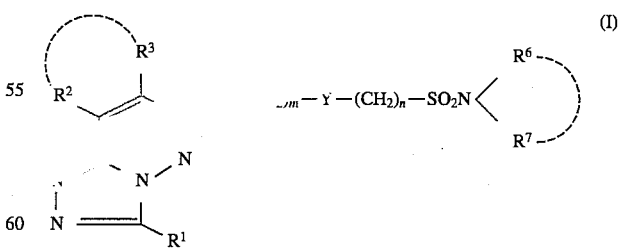

wherein $R^1$ represents a hydrogen atom, an optionally substituted lower alkyl group or a halogen atom; $R^2$ and $R^3$ independently represent a hydrogen atom or an optionally substituted lower alkyl group, or $R^2$ and $R^3$ together with the adjacent —C═C— may form a 5- to 7-membered ring; X represents an oxygen atom, a sulfur atom or a methylene group; Y represents (a) a group shown by the formula:

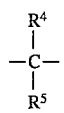

wherein $R^4$ and $R^5$ independently represent a hydrogen atom or an optionally substituted lower alkyl group, or (b) a divalent group derived from an optionally substituted 3- to 7-membered homo- or heterocyclic ring; $R^6$ and $R^7$ independently represent a hydrogen atom, an optionally substituted lower alkyl group, an optionally substituted cycloalkyl group or an optionally substituted aryl group, or $R^6$ and $R^7$ together with the adjacent nitrogen atom may form an optionally substituted nitrogen-containing heterocyclic group; m denotes an integer of 0 to 4; and n denotes an integer of 0 to 4, or a salt thereof.

It also provides a compound shown by the general formula (VI):

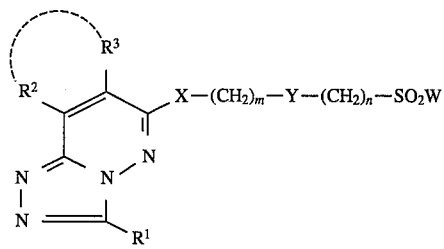

wherein $R^1$ represents a hydrogen atom, an optionally substituted lower alkyl group or a halogen atom; $R^2$ and $R^3$ independently represent a hydrogen atom or an optionally substituted lower alkyl group, or $R^2$ and $R^3$ together with the adjacent —C=C— may form a 5- to 7-membered ring; X represents an oxygen atom, a sulfur atom or a methylene group; Y represents (a) a group shown by the formula:

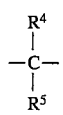

wherein $R^4$ and $R^5$ independently represent a hydrogen atom or an optionally substituted lower alkyl group, or (b) a divalent group derived from an optionally substituted 3- to 7-membered homo- or heterocyclic ring; m denotes an integer of 0 to 4; n denotes an integer of 0 to 4; and W represents a leaving group, or a salt thereof.

The invention further provides an antiasthmatic composition which comprises an effective amount of the compound of the general formula (I) or a salt thereof, and a pharmaceutically acceptable carrier.

The present invention still further provides an anti-platelet activating factor composition which comprises an effective amount of the compound of the general formula (I) or a salt thereof, and a pharmaceutically acceptable carrier.

The present invention further provides a method of producing a compound of the general formula (I) or a salt thereof, which comprises: reacting a compound shown by the general formula (II):

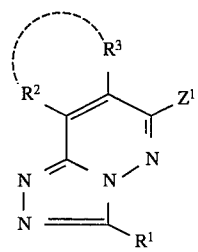

wherein $Z^1$ represents a reactive group; and $R^1$, $R^2$ and $R^3$ are as defined above, or a salt thereof, with a compound shown by the general formula (III):

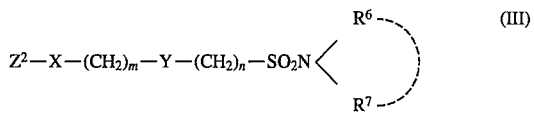

wherein $Z^2$ represents a leaving group which can be left on reacting with $Z^1$; and X, Y, $R^6$, $R^7$, m and n are as defined above, or a salt thereof.

The present invention further provides a method of producing the compound of the general formula (I) or a salt thereof, which comprises: reacting a compound shown by the general formula (IV):

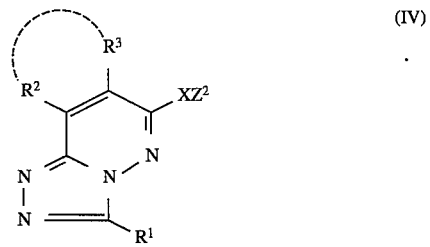

wherein $Z^2$ represents a leaving group which can be left on reacting with $Z^1$; and $R^1$, $R^2$, $R^3$ and X are as defined above, or a salt thereof, with a compound shown by the general formula (V):

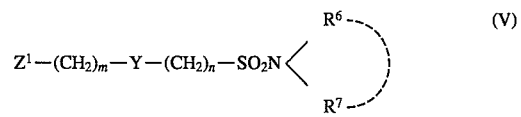

wherein $Z^1$ represents a reactive group; and Y, $R^6$, $R^7$, m and n are as defined above, or a salt thereof.

The present invention still further provides a method of producing the compound of the general formula (I) or a salt thereof, which comprises: reacting a compound shown by the general formula (VI):

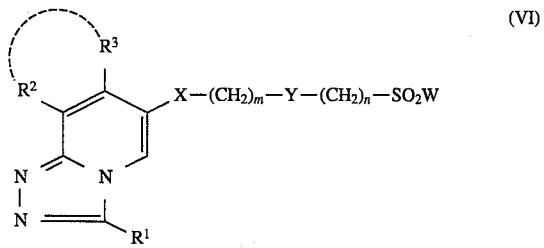

wherein W represents a leaving group; and $R^1$, $R^2$, $R^3$, X, Y, m and n are as defined above, or a salt thereof, with a compound shown by the general formula (VII):

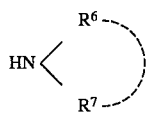

wherein $R^6$ and $R^7$ are as defined above, or a salt thereof.

The present invention also relates to a method for treating a disease caused by PAF (platelet activating factor) activity such as asthma which comprises administering a therapeutically effective amount of the compound of the formula (I) or a salt thereof together with a physiologically acceptable carrier, a method for inhibiting bronchoconstriction in a mammal by administering an anti-bronchoconstricting effective amount of the compound of the formula (I) or its salt to a mammal in need thereof, and a use of the compound of the formula (I) or a salt thereof as an effective component in the preparation of an anti-PAF composition or an anti-asthmatic composition.

When the compound shown by the formula (I) or a salt thereof has an asymmetric carbon in the structure, their optically active compounds and racemic mixtures are also included in the scope of the present invention.

DETAILED DESCRIPTION OF THE INVENTION

The term "lower alkyl group" as used in this specification means, for example, a straight or branched chain alkyl group having 1 to 6 carbon atoms. Examples of the $C_{1-6}$ alkyl group include methyl, ethyl, n-propyl, i-propyl, n-butyl, i-butyl, t-butyl, n-pentyl, n-pentyl and the like.

The term "cycloalkyl group" as used in this specification represents, for instance, a cycloalkyl group having 3 to 6 carbon atoms and so on. The $C_{3-6}$ cycloalkyl group includes, for example, cyclopropyl, cyclobutyl, cyclopentyl and cyclohexyl.

The term "aryl group" as used in this specification means, for example, an aryl group having 6 to 14 carbon atoms and others. Examples of the $C_{6-14}$ aryl group include phenyl and naphthyl.

As examples of the substituents which the "lower alkyl group" and "cycloalkyl group" may have, there may be mentioned a hydroxyl group, an amino group, a carboxyl group, a nitro group, a mono- or di-lower alkylamino group (e.g. a mono- or di-$C_{1-6}$ alkylamino group such as methylamino, ethylamino, propylamino, dimethylamino and diethylamino), a lower alkoxy group (for example, a $C_{1-6}$ alkoxy group such as methoxy, ethoxy, propoxy, i-propoxy, butoxy, i-butoxy, t-butoxy and hexyloxy), a lower acyloxy group (e.g. a $C_{1-6}$ alkylcarbonyloxy group such as acetoxy and propionyloxy) and a halogen atom (fluorine, chlorine, bromine or iodine atom). These substituents may substitute on the lower alkyl group or cycloalkyl group at any possible position, and two or more of such substituents may be the same or different. The number of these substituents is, for example, about 1 to 4.

Examples of the substituents for the "aryl group" include (1) an optionally substituted lower alkyl group, (2) an optionally substituted amino group, (3) an acetamido group, (4) a hydroxyl group, (5) a carboxyl group, (6) a nitro group, (7) a lower alkoxy group (for instance, a $C_{1-6}$ alkoxy group such as methoxy, ethoxy and propoxy), (8) an lower acyloxy group (e.g. a $C_{1-6}$ alkyl-carbonyloxy group such as acetoxy and propionyloxy) and (9) a halogen atom (e.g. fluorine, chlorine, bromine or iodine atom). These substituents may substitute on the aryl group at any possible position of the ring, and two or more of such substituents may be the same or different. The number of such substituents is, for instance, about 1 to 5.

The substituents which may optionally be substituted on the (1) lower alkyl group (e.g. a $C_{1-6}$ alkyl group such as methyl, ethyl and n-propyl) include, for example, a hydroxyl group, an amino group, a mono- or di-lower alkylamino group (e.g. a mono- or di-$C_{1-6}$ alkylamino group such as methylamino, ethylamino, propylamino, dimethylamino and diethylamino), a lower alkoxy group (for example, a $C_{1-6}$ alkoxy group such as methoxy, ethoxy, propoxy and hexyloxy) and a halogen atom (fluorine, chlorine, bromine or iodine atom). Example of the number of these substituents is about 1 to 4. The substituents for the (2) amino group may be exemplified with a $C_{1-6}$ alkyl group (e.g. methyl, ethyl, propyl, etc.). The number of these substituents is, for instance, about 1 or 2. When the amino group has two substituents, said substituents may form, taken together, a 5- to 7-membered cyclic amino group such as pyrrolidino, morpholino, piperidino and 1-piperazinyl.

The term "halogen atom" as used in this specification includes, for instance, fluorine, chlorine, bromine and iodine atoms.

The term "5- to 7-membered ring formed with the adjacent —C=C—" as used in this specification means (i) a 5- to 7-membered cyclic hydrocarbon ring or (ii) a 5- to 7-membered heterocyclic ring which have, other than carbon atom, 1 to 4 hetero atoms selected from, for example, a nitrogen atom, an oxygen atom, a sulfur atom and others. Typical examples of said ring include a 5- to 7-membered cyclic hydrocarbon such as a $C_{5-7}$ cycloalkene including cyclopentene, cyclohexene and cycloheptene, and benzene; a 5- or 6-membered nitrogen-containing heterocyclic ring having a carbon atom and a nitrogen atom such as pyrrole, pyridine, 1,2,3,4-tetrahydropyridine, 1,2,5,6-tetrahydropyridine and the like.

The term "3- to 7-membered homocyclic ring" as used in this specification represents, for instance, a 3- to 7-membered cyclic saturated or unsaturated hydrocarbon composed of carbon atoms. As practical examples of the 3- to 7-membered homocyclic ring, there may be mentioned a $C_{3-7}$ cycloalkane such as cyclopropane, cyclobutane, cyclopentane, cyclohexane and cycloheptane; a $C_{3-7}$ cycloalkene such as cyclopropene, cyclobutene, cyclopentene, cyclohexene and cycloheptene; and benzene.

The divalent group derived from the "3- to 7-membered homocyclic ring" means, for instance, a divalent group obtainable by removing two hydrogen atoms which bond to one carbon atom in said 3- to 7- membered cyclic hydrocarbon or respectively removing one hydrogen atom which bonds to each of two different carbon atoms in said cyclic hydrocarbon. Typical examples of said divalent group include such groups as follows:

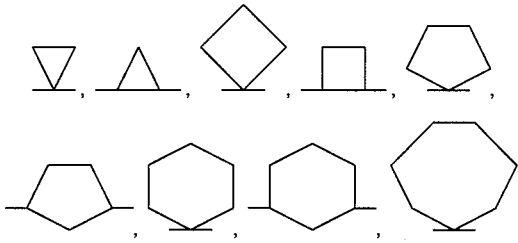

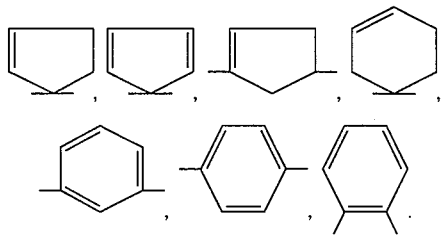

Preferred examples of the divalent group derived from the "3- to 7-membered homocyclic ring" include such groups as follows:

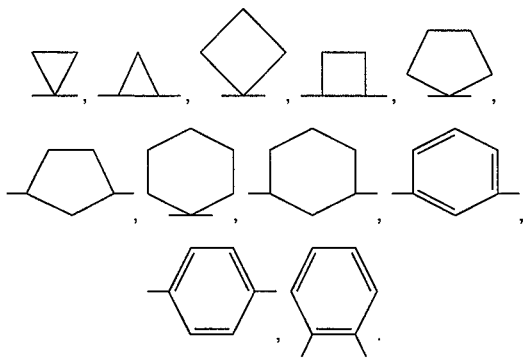

and more preferably those shown by the formula:

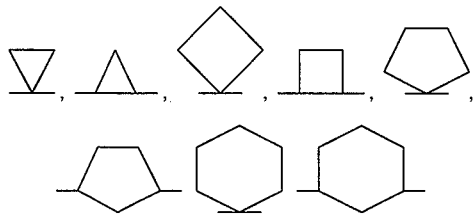

and most preferably those shown by the formula:

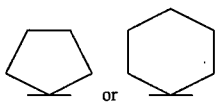

The term "3- to 7-membered heterocyclic ring" as used in this specification means, for example, a 3- to 7-membered heterocyclic ring having, other than a carbon atom, one to four hetero atoms selected from e.g. a nitrogen, oxygen, sulfur and other atoms. Typical examples of the 3- to 7-membered heterocyclic ring include oxetane, tetrahydrofuran, tetrahydropyran, pyrrole, azetidine, pyrrolidine, piperidine, piperazine, tetrahydrothiophene, homopiperidine, morpholine and the like.

The divalent group derived from the "3- to 7-membered heterocyclic ring" stands for a divalent group obtainable by removing two hydrogen atoms which bond to one carbon atom in said 3- to 7- membered heterocyclic ring or respectively removing one hydrogen atom which bonds to each of two different carbon atoms in said heterocyclic ring. To be specific, the following groups can be included by way of example:

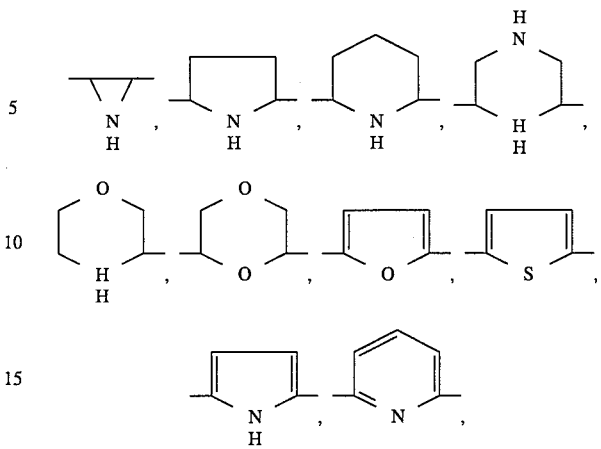

The term "nitrogen-containing heterocyclic group" as used in this specification represents, for example, a group obtainable by removing one hydrogen atom which bonds to a nitrogen atom on a ring such as a 3- to 13-membered nitrogen-containing heterocyclic ring having one nitrogen atom, which may further have one to three hetero atoms selected from nitrogen, oxygen, sulfur and other atoms. Typically, the nitrogen-containing heterocyclic group includes, for example, a 3- to 9-membered nitrogen-containing heterocyclic group of the formulae:

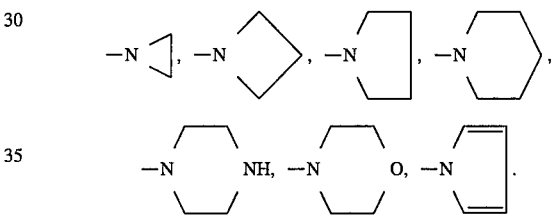

The substituents for the "3- to 7-membered homocyclic ring" "3- to 7-membered heterocyclic ring" and "nitrogen-containing heterocyclic group" are exemplified with (1) an optionally substituted lower alkyl group, (2) an optionally substituted amino group, (3) a hydroxyl group, (4) a carboxyl group, (5) a nitro group, (6) a lower alkoxy group (e.g. a $C_{1-6}$ alkoxy group such as methoxy, ethoxy and propoxy) and (7) a halogen atom (e.g. fluorine, chlorine, bromine or iodine atom). The number of these substituents is about one to five.

Examples of the substituents for the (1) lower alkyl group (for instance, a $C_{1-6}$ alkyl group such as methyl, ethyl and n-propyl) include a hydroxyl group, an amino group, a mono- or di-lower alkylamino group (e.g. a mono- or di-$C_{1-6}$ alkylamino group such as methylamino, ethylamino, propylamino, dimethylamino and diethylamino), a lower alkoxy group (for example, a $C_{1-6}$ alkoxy group such as methoxy, ethoxy, propoxy and hexyloxy), a lower acyloxy group (e.g. a $C_{1-6}$ alkyl-carbonyloxy group such as acetyloxy and propyloxy) and a halogen atom (e.g. fluorine, chlorine, bromine or iodine atom). The number of the substituents is, e.g., about one to four. As the substituents for the (2) amino group, there may be mentioned, for instance, a $C_{1-6}$ alkyl group such as methyl, ethyl, propyl group, etc., an acyl group (e.g. a $C_{1-6}$ acyl group such as formyl, acetyl, propionyl and butyryl) and others. The number of the substituents is about one or two. When the amino group has two substituents, the substituents may form, taken together, a 5- to 7-membered cyclic amino group (for instance, pyrrolidino, morpholino, piperidino, 1-piperazinyl, etc.) or the like.

In the compound shown by the formula (I), $R^1$ represents a hydrogen atom, an optionally substituted lower alkyl group or a halogen atom. Preferable example of $R^1$ include a halogen atom and a $C_{1-3}$ alkyl group such as methyl, ethyl, n-propyl, i-propyl group, etc. The compound wherein $R^1$ is a hydrogen atom has an specifically improved activity.

$R^2$ and $R^3$ independently represent a hydrogen atom or an optionally substituted lower alkyl group, or $R^2$ and $R^3$ together with the adjacent —C=C— to which they bond may form a 5- to 7-membered ring. Preferably, $R^2$ is a hydrogen atom, a $C_{1-3}$ alkyl group such as methyl, ethyl, n-propyl and i-propyl. A $C_{1-3}$ alkyl group can advantageously be employed as $R^2$ for a higher activity. Preferable examples of $R^3$ include a hydrogen atom and a $C_{1-3}$ alkyl group such as methyl, ethyl, n-propyl and i-propyl. Specifically preferred as $R^3$ is a hydrogen atom for a higher activity. Further, the case wherein $R^2$ and $R^3$, taken together with the adjacent —C=C—, form a 5- to 7-membered cyclic hydrocarbon is preferable, and to be specific, the case they form cyclohexene, benzene or the like is more preferable.

X represents an oxygen atom, a sulfur atom or a methylene group. Preferably, X is an oxygen atom or a sulfur atom, especially an oxygen atom.

Y represents (a) a group shown by the formula:

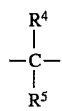

wherein $R^4$ and $R^5$ independently represent a hydrogen atom or an optionally substituted lower alkyl group, or (b) a divalent group derived from an optionally substituted 3- to 7-membered homo- or heterocyclic group. Practically preferred examples of Y include such groups as shown by the following formula:

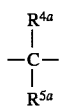

wherein $R^{4a}$ and $R^{5a}$ independently represent a hydrogen atom or an optionally substituted $C_{1-3}$ alkyl group.

The "$C_{1-3}$ alkyl group" represented by $R^{4a}$ and $R^{5a}$ includes, for instance, methyl, ethyl, n-propyl, i-propyl, etc. Examples of the "substituents" for said "$C_{1-3}$ alkyl group" include those used for the "lower alkyl group" as mentioned above. Preferably, $R^{4a}$ and $R^{5a}$ are independently a hydrogen atom or a $C_{1-3}$ alkyl group such as methyl, ethyl, n-propyl, etc. Specifically preferred examples of $R^{4a}$ and $R^{5a}$ include a $C_{1-3}$ alkyl group (e.g. methyl, ethyl, n-propyl, i-propyl, etc.).

Further, the compound where Y is a divalent group derived from an optionally substituted 3- to 7-membered homo- or heterocyclic ring is also preferable, and such divalent group include, for example;

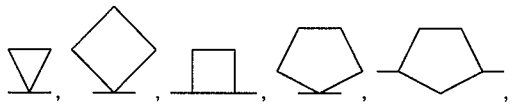

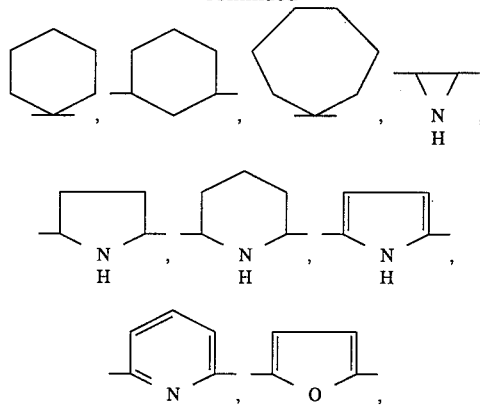

and more preferably,

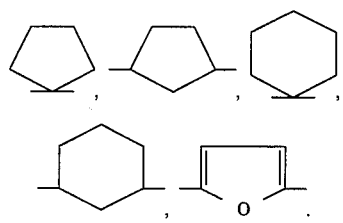

As preferable examples of the divalent group shown by Y derived from an optionally substituted 3- to 7-membered homo- or heterocyclic group, there may be mentioned:

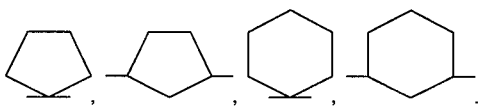

$R^6$ and $R^7$ independently represent a hydrogen atom, an optionally substituted lower alkyl group, an optionally substituted cycloalkyl group or an optionally substituted aryl group, or $R^6$ and $R^7$ together with the adjacent nitrogen atom to which they bond may form an optionally substituted nitrogen-containing heterocyclic group. Typical examples of $R^6$ and $R^7$ include a hydrogen atom, a $C_{1-3}$ alkyl such as methyl, ethyl, n-propyl, etc. Specifically preferred is a hydrogen atom for a higher activity.

m denotes an integer of 0 to 4. Preferably m is an integer of 1 to 4, more preferably an integer of 1 to 3, and specifically preferred is 1. n denotes an integer of 0 to 4, and preferably an integer of 1 to 4. The compounds having a higher activity include, among others, compounds wherein m is an integer of 1 and n is an integer of 1 to 4.

Preferable examples of the compounds include compounds where $R^1$, $R^2$ and $R^3$ independently represent a hydrogen atom or a $C_{1-3}$ alkyl group (e.g. methyl, ethyl, n-propyl, i-propyl); Y is (a) a group shown by the formula:

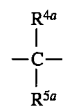

wherein $R^{4a}$ and $R^{5a}$ independently represent a hydrogen atom or an optionally substituted $C_{1-3}$ alkyl group (e.g. methyl, ethyl, n-propyl, i-propyl), or (b):

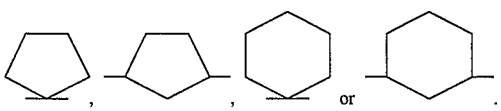,

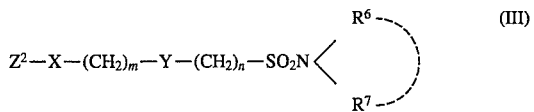

wherein $Z^2$, X, Y, $R^6$, $R^7$, m and n are as defined above, or a salt thereof.

$R^6$ and $R^7$ are independently a hydrogen atom or a $C_{1-3}$ alkyl group (e.g. methyl, ethyl, n-propyl, i-propyl); X is an oxygen atom; m denotes an integer of 1 to 3; and n denotes an integer of 1 to 4.

Typically preferred examples of the compounds include the compounds wherein $R^1$ is a hydrogen atom; $R^2$ and $R^3$ are independently a hydrogen atom or a $C_{1-3}$ alkyl group (e.g. methyl, ethyl, n-propyl, i-propyl); Y is a group shown by the formula:

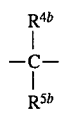

wherein $R^{4b}$ and $R^{5b}$ independently represent a $C_{1-3}$ alkyl group (e.g. methyl, ethyl, n-propyl, i-propyl); $R^6$ and $R^7$ are each a hydrogen atom; X is an oxygen atom; m is an integer of 1; and n is an integer of 1 to 4.

As salts of the compound of the formula (I) of this invention, physiologically acceptable acid addition salts are preferred. Examples of such salts include salts with inorganic acids (e.g. hydrochloric acid, phosphoric acid, hydrobromic acid, sulfuric acid, etc.), and salts with organic acids (for instance, acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

Further, where the compound of the formula (I) of the invention has an acidic group such as —COOH, the compound of the formula (I) may form a salt with an inorganic base (e.g. an alkali metal such as sodium, potassium, etc.; an alkaline earth metal such as calcium, magnesium, etc.; and ammonia) or with an organic base (e.g. a tri-$C_{1-3}$ alkylamine such as trimethylamine, triethylamine and the like), and these salts are involved in the subjects of the present invention.

In the following, the method of producing the compound of the formula (I) or a salt thereof of the present invention is described.

The compound (I) or a salt thereof can be obtained, for example, by (A) reacting a compound shown by the general formula (II):

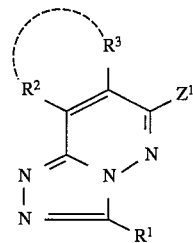

wherein $Z^1$, $R^1$, $R^2$ and $R^3$ are as defined above, or a salt thereof, with a compound shown by the general formula (III):

As the reactive group represented by $Z^1$, there may be mentioned, for instance, a halogen atom (e.9. chlorine, bromine or iodine atom), a $C_{6-10}$ azylsulfonyloxy group (for example, benzenesulfonyloxy, polylsulfonyloxy, etc.), a $C_{1-4}$ alkylsulfonyloxy group (e.g. methanesulfonyloxy) and so on.

The group shown by $Z^2$ which can be left on reacting with $Z^1$ includes, for example, a hydrogen atom, an alkali metal (e.g. sodium, potassium, etc.) and others.

The amount of the compound shown by the formula (III) or a salt thereof per mole of the compound shown by the formula (II) or a salt thereof as used in said reaction is, usually about 1 to 5 moles and preferably about 1 to 2 moles.

The condensation reaction can be advantageously conducted in the presence of a base. Examples of the base include an alkali metal hydride such as sodium hydride or potassium hydride, an alkali metal alkoxide such as sodium methoxide or sodium ethoxide, an alkali metal hydroxide such as sodium hydroxide or potassium hydroxide, a carbonate such as sodium carbonate or potassium carbonate, a hydrogen carbonate such as sodium hydrogen carbonate or potassium hydrogencarbonate.

This reaction can be carried out in an inert solvent including, for instance, alcohols such as methanol and ethanol, ethers such as dioxane and tetrahydrofuran, aromatic hydrocarbons such as benzene, toluene and xylene, nitriles such as acetonitrile, amides such as dimethylformamide and dimethylacetamide, sulfoxides such as dimethylsulfoxide, and others.

The reaction temperature is usually about 10° to 200° C. and preferably about 50° to 100° C. The reaction may be conducted for, usually, 30 minutes to 48 hours and preferably 1 to 24 hours.

The compound shown by the formula (I) or a salt thereof where X in the side chain is a methylene group can be obtained by reacting the compound shown by the formula (II) or a salt thereof with the compound shown by the formula (III) wherein the group represented by $Z^2$ is a halogenometalo group.

Practical examples of the group represented by $Z^1$ include a halogen atom (e.g. chlorine, bromine or iodine atom), a $C_{6-10}$ arylsulfonyloxy group (for example, benzenesulfonyloxy or p-tolylsulfonyloxy), a $C_{1-4}$ alkylsulfonyloxy group (for instance, methanesulfonyloxy) and the like.

As the halogen in the halogenometalo group represented by $Z^2$, there may be mentioned, for example, chlorine, bromine or iodine, and chlorine can advantageously be employed. The metal in the halogenometalo group includes, for example, zinc, magnesium, etc. and to be specific, zinc is preferable to be example.

This reaction can be preferably conducted by condensation in the presence of a palladium-catalyst. The palladium-catalyst means a catalyst which can be employed in the palladium-catalyst-crosscoupling reactions [such reactions are disclosed in Accounts of Chemical Research, 12, 146–151 (1979); ibid., 15, 340–348 (1982); Angew. Chem. Int. Ed. Engl., 25, 508–524 (1986), etc.], and is exemplified with a palladium-tertiary phosphine complex, a combination of a palladium salt or a palladium complex and a tertiary phosphine, and the like.

The palladium-tertiary phosphine complex means a complex formed with zero or divalent palladium and a tertiary phosphine such as a trialkylphosphine or a triarylphosphine. As examples of the palladium-tertiary phosphine complex, there may be mentioned tetrakis(triphenylphosphine)palladium, bis(triphenyl-phosphine)palladium bromide, bis(triphenylphosphine)palladium chloride, acetoxybis(triphenylphosphine)palladium, benzylchlorobis(triphenylphosphine)palladium, tetrakis(tributylphosphine)palladium, bis(trimethylphosphine)palladium chloride, bis(triethylphosphine)palladium chloride, bis(tripropylphosphine)palladium chloride, bis(tributylphosphine)palladium chloride, and so on.

Preferable examples of the palladium-tertiary phosphine complex include, for instance, tetrakis (triphenylphosphine)palladium, bis(triphenylphosphine)palladium bromide, bis(triphenylphosphine)palladium chloride and acetoxybis(triphenylphosphine)palladium.

The palladium salt signifies a salt formed with a divalent palladium ion and an acid residue and includes, for instance, palladium chloride, palladium bromide, palladium acetate, palladium nitrate, palladium sulfate and others. Typically preferred palladium salt are exemplified with palladium chloride, palladium bromide and palladium acetate.

As the palladium complex, other zero or divalent palladium complex than the palladium-tertiary phosphine complex as above can also be employed. As such palladium complex, there may be mentioned, for example, bis(phenylethylamine)palladium chloride, bis(benzonitrile)palladium chloride, bis(benzonitrile)palladium bromide or bis(acetonitrile)palladium chloride. Among them, for instance, bis(benzonitrile)palladium chloride and bis(acetonitrile)palladium chloride can advantageously be used.

Examples of the tertiary phosphine include a triarylphosphine such as triphenylphosphine, a trialkylphosphine such as tributylphosphine, tripropylphosphine, triethylphosphine, trimethylphosphine, etc. A triarylphosphine such as triphenylphosphine can preferably be employed as the tertiary phosphine.

The reaction can preferably be carried out in the presence of a solvent. The solvent includes, for example, aromatic hydrocarbons such as benzene, toluene or xylene; ethers such as diethyl ether, tetrahydrofuran or dioxane; amides such as dimethylformamide or dimethylacetamide; sulfoxides such as dimethylsulfoxide; and nitriles such as acetonitrile.

The reaction may be conducted at a temperature of usually about 0° to 200° C. and preferably about 10° to 100° C. The reaction time is, generally, about 30 minutes to 24 hours and preferably about 1 to 3 hours. This reaction can advantageously be carried out in a stream of an inert gas such as nitrogen or argon.

The product can be isolated and purified by a conventional manner such as solvent extraction, phasic transfer or change of acidity or basicity, elution, solvent transfer or redistribution, salting out, crystallization, recrystallization, chromatography and the like.

The compound shown by the general formula (I) or a salt thereof can also be produced by (B) reacting a compound of the general formula (IV):

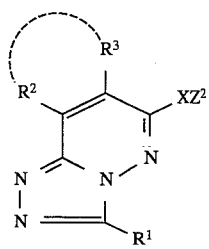
(IV)

wherein $Z^2$, $R^1$, $R^2$, $R^3$ and X are of the same meaning as defined above, or a salt thereof, with a compound shown by the general formula (V):

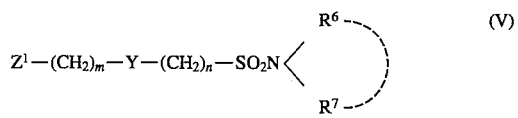
(V)

wherein $Z^1$, Y, $R^6$, $R^7$, m and n are as defined above, or a salt thereof.

In the reaction, the compound of the formula (V) or a salt thereof is used, per mole of the compound of the formula (IV) or a salt thereof, in a proportion of usually about 1 to 5 moles and preferably about 1 to 2 moles.

The condensation reaction can advantageously be conducted, usually, in the presence of a base. As the base, there may be mentioned, for instance, an alkali metal hydride such as sodium hydride or potassium hydride, an alkali metal alkoxide such as sodium methoxide or sodium ethoxide, an alkali metal hydroxide such as sodium hydroxide or potassium hydroxide, a carbonate compound such as sodium carbonate or potassium carbonate, a hydrogencarbonate compound such as sodium hydrogencarbonate or potassium hydrogencarbonate, and the like.

This reaction may be carried out in an inert solvent including, for example, alcohols such as methanol and ethanol; ethers such as dioxane and tetrahydrofuran; aromatic hydrocarbons such as benzene, toluene and xylene; nitriles such as acetonitrile; amides such as dimethylformamide and dimethylacetamide; sulfoxides such as dimethylsulfoxide.

The reaction temperature is generally about 10° to 200° C. and preferably about 50° to 150° C., and the reaction can be conducted for, usually, 30 minutes to 24 hours and preferably 1 to 10 hours.

Further, the compound shown by the formula (I) or a salt thereof may also be obtained by (C) reacting a compound shown by the general formula (VI):

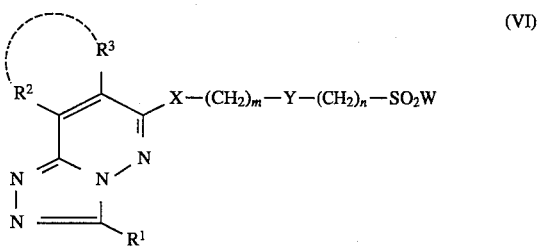
(VI)

wherein W, $R^1$, $R^2$, $R^3$, X, Y, m and n are as defined above, or a salt thereof, with a compound shown by the general formula (VII):

(VII)

wherein $R^6$ and $R^7$ are of the same meanings as defined above, or a salt thereof.

Examples of the leaving group represented by W include a halogen atom (e.g. chlorine, bromine or iodine atom), a $C_{6-10}$ arylsulfonyloxy group (for instance, benzenesulfonyloxy or p-tolylsulfonyloxy), a $C_{1-4}$ alkylsulfonyloxy group (e. g. methanesulfonyloxy, etc.) and others. A halogen atom (e.g. chlorine, bromine or iodine atom) is preferred among others.

The amount of the compound of the formula (VII) or a salt thereof used in the reaction is, usually, about 1 to 5 moles and preferably about 1 to 2 moles per mole of the compound of the formula (VI) or a salt thereof.

This reaction may frequently be carried out in an inert solvent such as, for example, alcohols including methanol and ethanol; ethers including dioxane and tetrahydrofuran; aromatic hydrocarbons including benzene, toluene and xylene; nitriles including acetonitrile; amides including dimethylformamide and dimethylacetamide; sulfoxides including dimethylsulfoxide.

The reaction can be conducted at a temperature of, generally, about −20° C. to 100° C. and preferably about −10° C. to 50° C., for usually about 30 minutes to 5 hours and preferably about 1 to 3 hours.

Where the resulting compound of the formula (I) thus obtained above is in a free form, it may be led to a salt thereof by a conventional means or those analogous thereto. Conversely, when the compound is obtained in the form of a salt, it may be led to the free compound or any other salt by a conventional method.

The compound of the formula (I) or its salt can be isolated and purified by a conventional technique such as solvent extraction, phasic transfer or change of acidity or basicity, elution, solvent transfer or redistribution, salting out, crystallization, recrystallization, or other techniques. Where the compound of the formula (I) or its salt is an optically active compound, it may be isolated to d-form and l-form by a conventional means for optical resolution.

The methods of producing the starting compounds shown by the formulae (II), (III), (IV), (V), (VI) and (VII) or salts thereof as used in the production of the compound of the formula (I) or a salt thereof are mentioned hereinbelow.

As examples of the salts of these compounds, there may be mentioned salts with inorganic acids (e.g. hydrochloric acid, phosphoric acid, hydrobromic acid, sulfuric acid, etc.), and salts with organic acids (for instance, acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

Further, when the compounds have an acidic group such as —COOH, these compounds may form a salt with an inorganic base (e.g. an alkali metal such as sodium, potassium, etc.; an alkaline earth metal such as calcium, magnesium, etc.; and ammonia) or with an organic base (e.g. a tri-$C_{1-3}$ alkylamine such as trimethylamine, triethylamine and the like).

The starting compounds of the formula (II) or its salt can be prepared, for instance, by the method stated in *Chem. Pharm. Bull.*, 5, 229 (1957), or those analogous thereto.

The starting compounds of the formulae (III) and (V) or their salt can be prepared, for example, by the methods disclosed in e.g. *Chem. Ber.*, 91, 2130 (1958); *J. Org. Chem.*, 52, 2162 (1987); Japanese Patent Application Laid-open No. 223287/1991, or analogous ones thereto.

The compound of the formula (IV) or a salt thereof may be prepared by, for instance, the method disclosed in Japanese Patent Application Laid-open No. 223287/1991 or those analogous thereto.

The starting compound (VI) or its salt can be prepared by, for example, the following methods (a) or (b);

(a) the method reacting the compound of the formula (II) or a salt thereof with a compound of the following formula:

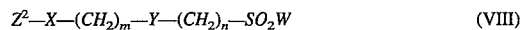

$$Z^2-X-(CH_2)_m-Y-(CH_2)_n-SO_2W \qquad (VIII)$$

wherein $Z^2$, X, Y, W, m and n are as defined above, (b) the method reacting the compound of the formula (IV) or a salt thereof with a compound shown by the following formula:

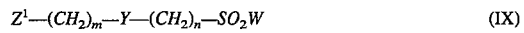

$$Z^1-(CH_2)_m-Y-(CH_2)_n-SO_2W \qquad (IX)$$

wherein $Z^1$, Y, W, m and n are of the same meanings as defined above.

In the reaction (a), the using amount of the compound of the formula (VIII) is usually about 1 to 5 moles and preferably about 1 to 2 moles, per mole of the compound of the formula (II) or its salt. The reaction can be carried out under the conditions similar to those in the reaction of the compound of the formula (II) or its salt with the compound of the formula (III) or its salt as mentioned above.

The compound of the formula (IX) is used in a proportion of, per mole of the compound (IV) or its salt, usually about 1 to 5 moles and preferably about 1 to 2 moles in the reaction (b). The reaction can be carried out in the manner similar to those in the reaction of the compound of the formula (IV) or a salt thereof with the compound of the formula (V) or a salt thereof.

The starting compound of the formula (VII) or a salt thereof, and the starting compounds of the formulae (VIII) and (IX) can be produced by a conventionally known method or analogous ones thereto.

These starting compounds or their salts can be isolated and purified by a conventional manner such as solvent extraction, phasic transfer, change of acidity or basicity, elution, solvent transfer, redistribution, salting out, crystallization or recrystallization, or they may be fed to the subsequent process as the material in the state of mixture without isolation.

In each reaction of the invention and the production of the starting compounds, when the starting compound has, as substituent(s), an amino group, a carboxyl group or a hydroxyl group, these groups may be protected with such protecting groups as generally used in peptide chemistry, and the object compound may be obtained by, if necessary, removing these protecting groups after the reaction.

As examples of the protecting groups for amino group, there may be mentioned a formyl group, a $C_{1-6}$ alkyl-carbonyl group (e.g. acetyl, propionyl, etc.), a benzoyl group, a $C_{1-6}$ alkyl-oxycarbonyl group (e.g. methoxycarbonyl, ethoxycarbonyl, etc.), a phenoxycarbonyl group, a $C_{7-10}$ aralkyl-carbonyl group (for instance, benzylcarbonyl, etc.), a trityl group, a phthaloyl group, an N,N-dimethylaminomethylene group, an N,N-diethylaminomethylene group and so on which may be substituted. Examples of the substituents which these protecting groups may have include a halogen atom (e.g. fluorine, chlorine, bromine or iodine atom), a $C_{1-6}$ alkyl-carbonyl group (e.g. acetyl, propionyl, butyryl, etc.), a nitro group and the like. The number of these substituents is from about 1 to 3.

The protecting group for carboxyl group include, for example, a $C_{1-6}$ alkyl group (e.g. methyl, ethyl, n-propyl, i-propyl, n-butyl, tert-butyl, etc.), a phenyl group, a trityl group, a silyl group and so on which may optionally be substituted. As examples of the substituents for these protecting groups, there may be mentioned a halogen atom (e.g.

fluorine, chlorine, bromine or iodine atom), a formyl group, a $C_{1-6}$ alkylcarbonyl group (e.g. acetyl, propionyl, butyryl, etc.), a nitro group and so on. The number of these substituents is from about 1 to 3.

Examples of the protecting group of hydroxyl group include a $C_{1-6}$ alkyl group (for example, methyl, ethyl, n-propyl, i-propyl, n-butyl, tert-butyl, etc.), a phenyl group, a $C_{7-10}$ aralkyl group (e.g. benzyl, etc.), a formyl group, a $C_{1-6}$ alkyl-carbonyl group (e.g. acetyl, propionyl, etc.), a phenoxycarbonyl group, a benzoyl group, a $C_{7-10}$ aralkyl-carbonyl group (e.g. benzylcarbonyl, etc.), a pyranyl group, a furanyl group, a silyl group and others which may be substituted. Examples of the substituents for these protecting groups include a halogen atom (e.g. fluorine, chlorine, bromine or iodine atom), a $C_{1-6}$ alkyl group (for instance, methyl, ethyl, n-propyl, etc.), a phenyl group, a $C_{7-10}$ aralkyl group (e.g. benzyl, etc.), a nitro group and the like. The number of these substituents varies from about 1 to 4.

As the means of removing these protecting group, conventionally known means or those analogous thereto are employed. Examples of such means include those which comprise processing with an acid, a base, reduction, ultraviolet-ray radiation, or treating with hydrazine, phenylhydrazine, sodium N-methyldithiocarbamate, tetrabutylammonium fluoride, palladium acetate, or the like.

The compound of the formula (I) or a salt thereof has excellent antiallergic, antiinflammatory and anti-PAF (platelet activating factor) activities, and has a lower toxicity (the acute toxicity: $LD_{50}$ is more than 1 g/kg), thus is useful as a safely administrable agent as an antiasthmatic agent and/or an anti-PAF agent to mammals such as human being, mouse, dog, rat, cattle or others.

Although the compound of the general formula (I) or its salt of the present invention may be administered as such in the form of bulk powder, it is a common practice to administer it in the form of a pharmaceutical preparation along with pharmaceutically acceptable carriers.

Such pharmaceutical preparations include, for example, tablets, capsules, granules, fine granules, powders, syrups, injections and inhalations. These pharmaceutical preparations may be prepared by conventionally known methods. Examples of the carriers of the pharmaceutical preparations for oral administration include various substances generally used in pharmaceutical preparations for oral administration such as binders, excipients, disintegrators and the like. These carriers include, for instance, starch, mannitol, crystalline cellulose, sodium carboxymethylcellulose and others. As the carriers for injections, there may be mentioned, for example, distilled water, physiological saline solution, glucose solution, infusion agent and so on. Other additives commonly used in the pharmaceutical preparations can be suitably added to the above mentioned pharmaceutical preparations.

While depending on the age, body weight, type and symptom of diseases to be treated, route of administration or administration time, the dose of these pharmaceutical preparations to adult humans per day is, for instance, usually about 0.1 to 100 mg/kg, preferably about 1 to 50 mg/kg and more preferably about 1 to 10 mg/kg. The administration may advantageously be carried out once a day or in a plurality of installments per day. These pharmaceutical preparation can be administered orally or non-orally.

EXAMPLES

By the following examples, preparation examples and experimental examples, the present invention will be illustrated in more concrete manner, but they should by no means be construed as defining the metes and bounds of this invention.

In the examples, elution in the procedure of column chromatography was carried out under observation by means of TLC (Thin Layer Chromatography) unless otherwise specified. In the TLC observation, $60F_{254}$ manufactured by Merck as the TLC plate, and a UV detector was employed for detection. The term "ambient temperature" or "room temperature" generally means temperatures ranging from about 15° to 20° C.

EXAMPLE 1

Production of 6-(2,2-diethyl-3-sulfamoyl-1-propoxy)-8-methyl-[1,2,4]triazolo[4,3-b]pyridazine To a solution of 1.38 g of 3-(N,N-dimethylaminomethylene)aminosulfonyl-2,2-diethyl-1-propanol in 30 ml of tetrahydrofuran, was added 0.23 g of 60% oily sodium hydride, and the mixture was stirred at room temperature for one hour. To the reaction mixture was added 0.74 g of 6-chloro-8-methyl-[1,2,4]triazolo[4,3-b]pyridazine, and the mixture was heated under reflux at 80° C. for 40 hours. The reaction mixture was added with 50 ml of ice-water, and subsequently, 15 ml of 1 N hydrochloric acid, and the resulting mixture was refluxed for one hour.

The reaction mixture was neutralized with 2 N aqueous solution of sodium hydroxide, and extracted with a mixture of ethyl acetate-tetrahydrofuran (2:1). The extract was washed with a saturated sodium chloride solution, dried over anhydrous magnesium sulfate, and was distilled under reduced pressure to remove the solvent. The residue was subjected to a column chromatography with the use of 100 g of silica gel, eluting with methanol-chloroform (1:10) to give 0.88 g of the title compound.

m.p. 209° to 210° C.

Elemental analysis for $C_{13}H_{21}N_5O_3S$: Calculated (%): C, 47.69; H, 6.46; N, 21.39 Found (%): C, 47.61; H, 6.67; N, 21.25

EXAMPLE 2

Production of 6-(2,2-diethyl-3-sulfamoyl-1-propoxy)-7-methyl-[1,2,4]triazolo[4,3-b]pyridazine 3-(N,N-dimethylaminomethylene)aminosulfonyl-2,2-diethyl-1-propanol (0.5 g) was dissolved in 20 ml of tetrahydrofuran, to which 0.09 g of 60% oily sodium hydride, and the mixture was stirred for 1 hour at room temperature. To the reaction mixture was added 0.3 g of 6-chloro-7-methyl-[1,2,4]triazolo[4,3-b]pyridazine, and the mixture was heated and refluxed at 80° C. for 40 hours.

The reaction mixture was added with water and extracted with ethyl acetate. The extract was washed with water, dried over anhydrous magnesium sulfate, and distilled under reduced pressure to remove the solvent. The residue was subjected to a column chromatography using 80 g of silica gel, eluting with methanol-chloroform (1:20) to give 0.24 g of 6-[2,2-diethyl-3-(N,N-dimethylaminomethylene)aminosulfonyl-1-propoxy]-7-methyl-[1,2,4]triazolo[4,3-b]pyridazine.

The compound thus obtained was added to 7 ml of 6 N hydrochloric acid and the mixture was stirred at 100° C. for half an hour. The reaction mixture was neutralized with 2 N aqueous solution of sodium hydroxide and extracted with a mixture of ethyl acetate-tetrahydrofuran (2:1). The extract was washed with a saturated sodium chloride solution, dried over anhydrous magnesium sulfate, and the solvent was distilled off under reduced pressure. The residue was subjected to a column chromatography with the use of 60 g of silica gel, eluting methanol-chloroform (1:10) to give 0.11 g of the title compound.

m.p.: 202° to 203° C.

Elemental analysis for $C_{13}H_{21}N_5O_3S$ Calculated (%): C, 47.69; H, 6.46; N, 21.39 Found (%): C, 47.40; H, 6.54; N, 21.12

EXAMPLE 3

Production of 6- (2,2-diethyl-3-sulfamoyl-1-propoxy)[1, 2, 4]triazolo[4,3-b]pyridazine The procedures of Example 1 were repeated by using 3-(N, N-diethylaminomethylene) aminosulfonyl-2,2-diethyl-1-propanol and 6-chloro-[1,2,4]triazolo[4,3-b]pyridazine to give the title compound.

m.p.: 242° to 243° C.

Elemental analysis for $C_{12}H_{19}N_5O_3S$ Calculated (%): C, 45.99; H, 6.11; N, 22.35 Found (%): C, 45.84; H, 6.24; N, 22.34

EXAMPLE 4

Production of 6-(2,2-dimethyl-3-sulfamoyl-1-propoxy)-7-methyl-[1,2,4]triazolo[4,3-b]pyridazine The title compound was obtained in the same manner as in Example 1 by using 3-(N,N-dimethylaminomethylene) aminosulfonyl-2,2-dimethyl-1-propanol and 6-chloro-7-methyl-[1,2,4]triazolo[4,3-b]pyridazine.

m.p.: 259° to 260° C.

Elemental analysis for $C_{11}H_{17}N_5O_3S$ Calculated (%): C, 44.14; H, 5.72; N, 23.39 Found (%): C, 44.17; H, 5.83; N, 22.88

EXAMPLE 5

Production of 6- (2,2-dimethyl-3-sulfamoyl-1-propoxy)[1,2,4]triazolo[4,3-b]pyridazine The procedures of Example 1 were repeated except that 3-(N,N-dimethylaminomethylene)aminosulfonyl-2,2-dimethyl-1-propanol and 6-chloro-[1,2,4]triazolo[4,3-b]pyridazine were employed to give the title compound.

m.p.: 199° to 200° C.

Elemental analysis for $C_{10}H_{15}N_5O_3S$ Calculated (%): C, 42.10; H, 5.30; N, 24.55 Found (%): C, 42.13; H, 5.50; N, 24.62

EXAMPLE 6

Production of 6-(2,2-pentamethylene-4-sulfamoyl-1-butoxy)[1,2,4]triazolo[4,3-b]pyridazine The title compound was obtained in the same manner as in Example 1 by using 4-(N,N-dimethylaminomethylene) aminosulfonyl-2,2-pentamethylene-1-butanol and 6-chloro-[1,2,4]triazolo[4,3-b]pyridazine.

m.p.: 201° to 203° C.

Elemental analysis for $C_{14}H_{21}N_5O_3S$ Calculated (%): C, 49.54; H, 6.24; N, 20.63 Found (%): C, 49.46; H, 6.44; N, 20.22

PREPARATION EXAMPLE 1

(1) Compound of Example 1 10.0 mg
(2) Lactose 60.0 mg
(3) Corn starch 35.0 mg
(4) Gelatin 3.0 mg
(5) Magnesium stearate 2.0 mg Using 0.03 ml of a 10% aqueous solution of gelatin (3.0 mg as gelatin), a mixture of 10.0 mg of the compound of Example 1, 60.0 mg of lactose and 35.0 mg of corn starch was granulated by passage through a 1 mm-mesh sieve to obtain granules. The granules were dried at 40° C. and screened again. The resulting granules were mixed with 2.0 mg of magnesium stearate, and the mixture were compressed. The resulting core tablets were sugar-coated with an aqueous suspension containing sucrose, titanium dioxide, talc and gum arabic. The resulting tablets were glazed with beeswax to give a coated tablet.

PREPARATION EXAMPLE 2

(1) Compound of Example 1 10.0 mg
(2) Lactose 70.0 mg
(3) Corn starch 50.0 mg
(4) Soluble starch 7.0 mg
(5) Magnesium stearate 3.0 mg A mixture of the compound of Example 1 (10.0 mg) and magnesium stearate (3.0 mg) was granulated using an aqueous solution of 0.07 ml of soluble starch (7.0 mg as soluble starch) to give granules. The granules were dried and blended with 70.0 mg of lactose and 50.0 mg of corn starch. The blend was compressed into a tablet.

PREPARATION EXAMPLE 3

(1) Compound of Example 1 5.0 mg
(2) Sodium chloride 20.0 mg
(3) Distilled water added to 2.0 ml Compound of Example 1 (5.0 mg) and sodium chloride (20.0 mg) were dissolved in distilled water, to which distilled water was added up to the total volume of 2.0 ml. The resulting solution was filtered and filled into a 2 ml-ampule under a sterile condition. The ampule was sterilized and sealed to give an injection solution.

EXPERIMENTAL EXAMPLE 1

[Effect on bronchoconstriction induced by platelet activating factor (PAF) in guinea pigs]

Male Hartley guinea pigs (body weights about 500 g) were used. The bronchoconstriction reaction in the guinea pig which has intravenously been administered with PAF (1 µg/kg) was measured by the Konzett-Roessler method.

The trachea of the guinea pig with its back fixed was incised under anesthesia condition with urethane (intravenous injection, 1.5 g/kg) and connected with an artificial respirator via a cannula. The branch of the tracheal cannula was connected with a transducer (7020 type, manufactured by Ugobasile). Air was sent to the trachea at the rate of 3 to 7 ml per stroke, 70 strokes/min. and at load pressure of 10 cm $H_2O$ to lung, and overflowed air volume was recorded with Rectegraph (Recte-Hori-8s, Sanei Sokuki Co., Ltd., Japan) via transducer. After the guinea pig was treated with gallamine (intravenous injection, 1 mg/kg), 1 µg/kg of PAF dissolved in a physiological saline solution was administered to the guinea pig via jugular venous cannula and the bronchoconstriction reaction induced thereby was recorded for 15 minutes. The drug (3 mg/kg and 10 mg/kg respectively) suspended in a 5% gum arabic solution was administered orally 1 hour before the injection of PAF. The results are shown in Table 1.

TABLE 1

| Example No. | Inhibition (%) of PAF-induced bronchoconstriction Amount of oral administration | |
|---|---|---|
| | 3 mg/kg | 10 mg/kg |
| 1 | 85.8 | 100 |
| 2 | — | — |
| 3 | 51.1 | 61.2 |
| 4 | — | — |
| 5 | 22.4 | 41.2 |
| 6 | — | — |

As clearly shown in the above Table 1, the compound shown by the formula (I) or its salt of the present invention has an excellent anti-PAF (platelet activating factor) action.

What is claimed is:

1. A compound of the formula:

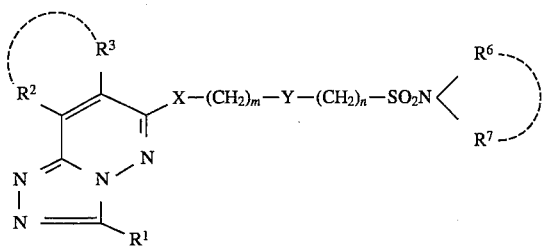

wherein $R^1$ represents (i) a hydrogen atom, (ii) a $C_{1-6}$ alkyl group which may have one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom or (iii) a halogen atom;

$R^2$ and $R^3$ independently represent a hydrogen atom or a $C_{1-6}$ alkyl group which may have one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom;

X represents an oxygen atom, a sulfur atom or a methylene group;

Y represents (a) a group shown by the formula:

wherein $R^4$ and $R^5$ independently represent a hydrogen atom or a $C_{1-6}$ alkyl group which may have one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom, or (b) divalent group selected from the group consisting of the formula:

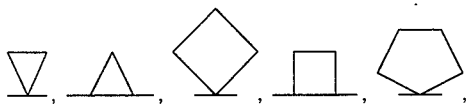

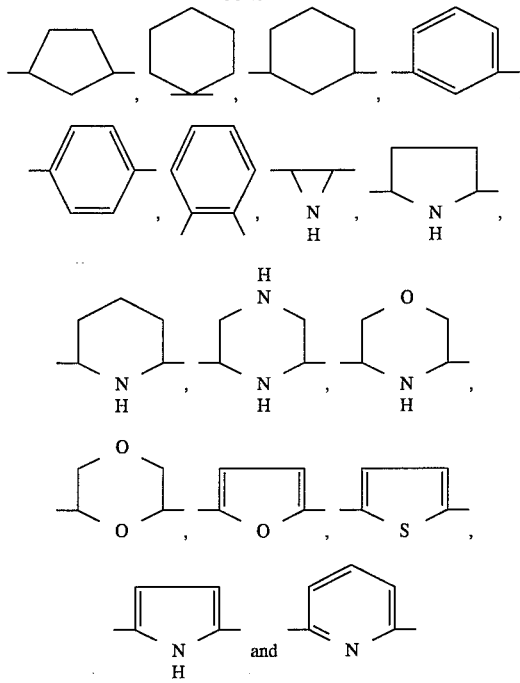

which may be substituted with one to five substituents selected from the group consisting of (i) a $C_{1-6}$ alkyl group which may be substituted with one to four substituents selected from the group consisting of a hydroxyl group, an amino group, a mono- or di-$C_{1-6}$ alkylamino group, a $C_{1-6}$ alkoxy group, a $C_{1-6}$ alkyl-carbonyloxy group and a halogen atom, (ii) an amino group which may be substituted with one to two substituents selected from a $C_{1-6}$ alkyl group and a $C_{1-6}$ acyl group, or a pyrrolidino, a morpholine, a piperidino or a 1-piperazinyl group, (iii) a hydroxyl group, (iv) a carboxyl group, (v) a nitro group, (vi) a $C_{1-6}$ alkoxy group and (vii) a halogen atom;

$R^6$ and $R^7$ independently represent (1) a hydrogen atom, (2) a $C_{1-6}$ alkyl group which may have one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom, (3) a $C_{3-6}$ cycloalkyl group which may be substituted with one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom, or (4) a $C_{6-14}$ aryl group which may be substituted with one to five substituents selected from the group consisting of (a) a $C_{1-6}$ alkyl group which may be substituted with one to four substituents selected from the group consisting of a hydroxyl group, an amino group, a mono-or di-$C_{1-6}$ alkylamino group, a $C_{1-6}$ alkoxy group, and a halogen atom, (b) an amino group which may be substituted with one or two $C_{1-6}$ alkyl groups, or a pyrrolidino, a morpholino, a piperidino or a 1-piperazinyl group, (c) an acetamido group, (d) a hydroxyl group, (e) a carboxyl group, (f) a nitro group, (g) a $C_{1-6}$ alkoxy group, (h) a $C_{1-6}$ alkyl-carbonyloxy group and (i) a halogen atom, or (5) $R^6$ and $R^7$ together with the adjacent nitrogen atom may form a nitrogen-containing heterocyclic group selected from the group consisting of:

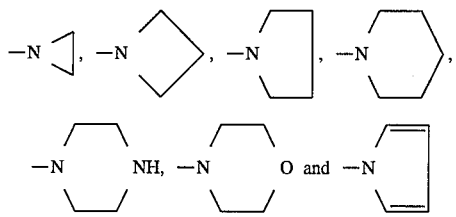 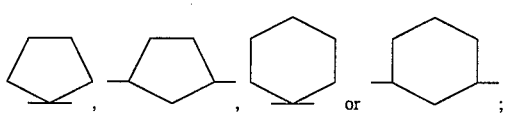

which may be substituted with one to five substituents selected from the group consisting of (i) a $C_{1-6}$ alkyl group which may be substituted with one to four substituents selected from the group consisting of a hydroxyl group, an amino group, a mono- or di-$C_{1-6}$ alkylamino group, a $C_{1-6}$ alkoxy group, a $C_{1-6}$ alkyl-carbonyloxy group and a halogen atom, (ii) an amino group which may be substituted with one to two substituents selected from a $C_{1-6}$ alkyl group and a $C_{1-6}$ acyl group, or a pyrrolidino, a morpholino, a piperidino or a 1-piperazinyl group, (iii) a hydroxyl group, (iv) a carboxyl group, (v) a nitro group, (vi) a $C_{1-6}$ alkoxy group and (vii) a halogen atom; m denotes an integer of 0 to 4; and n denotes an integer of 0 to 4, or a pharmaceutically acceptable salt thereof.

2. A compound as claimed in claim 1, wherein $R^1$ represents a hydrogen atom or a $C_{1-3}$ alkyl group.

3. A compound as claimed in claim 1, wherein $R^1$ represents a hydrogen atom.

4. A compound as claimed in claim 1, wherein $R^6$ and $R^7$ independently represent a hydrogen atom or a $C_{1-3}$ alkyl group.

5. A compound as claimed in claim 1, wherein X is an oxygen atom.

6. A compound as claimed in claim 1, wherein m denotes an integer of 1 to 3 and n denotes an integer of 1 to 4.

7. A compound as claimed in claim 1, wherein $R^1$ is a hydrogen atom; $R^2$ and $R^3$ are independently a hydrogen atom or a $C_{1-3}$ alkyl group; Y is a group shown by the formula:

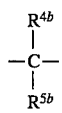

wherein $R^{4b}$ and $R^{5b}$ independently represent a $C_{1-3}$ alkyl group; $R^6$ and $R^7$ are a hydrogen atom; X is an oxygen atom; m is 1; and n is an integer of 1 to 4.

8. A compound as claimed in claim 1, wherein $R^2$ and $R^3$ independently represent a hydrogen atom or a $C_{1-3}$ alkyl group.

9. A compound as claimed in claim 1, wherein $R^1$, $R^2$ and $R^3$ are independently a hydrogen atom or a $C_{1-3}$ alkyl group; Y is (a) a group shown by the formula:

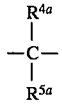

wherein $R^{4a}$ and $R^{5a}$ independently represent a hydrogen atom or a $C_{1-3}$ alkyl group which may have one to four substituents selected from the group consisting of a hydroxyl group, an amino group, a mono- or di-$C_{1-6}$ alkylamino group, a $C_{1-6}$ alkoxy group, a $C_{1-6}$ alkyl-carbonyloxy group and a halogen atom, or (b) a group shown by the formula:

$R^6$ and $R^7$ are independently a hydrogen atom or a $C_{1-3}$ alkyl group; X is an oxygen atom; m is an integer of 1 to 3; and n is an integer of 1 to 4.

10. A compound as claimed in claim 1, which is selected from the group consisting of (1) 6-(2,2-diethyl-3-sulfamoyl-1-propoxy)-8-methyl-1,2,4]triazolo[4,3-b]pyridazine or a salt thereof, (2) 6-(2,2-diethyl-3-sulfamoyl-1-propoxy)[1,2,4]triazolo[4,3-b]pyridazine or a salt thereof, and (3) 6-(2,2-dimethyl-3-sulfamoyl-1-propoxy)[1,2,4]triazolo[4,3-b]pyridazine or a salt thereof.

11. A compound of the formula:

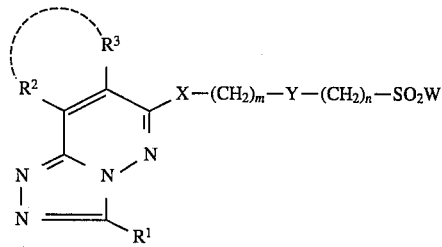

wherein W represents a halogen atom, a $C_{6-10}$ arylsulfonyloxy group or a $C_{1-4}$ alkylsulfonyloxy group, wherein $R^1$ represents (i) a hydrogen atom, (ii) a $C_{1-6}$ alkyl group which may have one to four substituents selected from the group consisting of a hydroxyl group, an amino group a carboxyl group, a nitro group, a mono- or di-$C_{1-6}$ alkylamino group, a $C_{1-6}$ alkoxy group, a $C_{1-6}$ alkyl-carbonyloxy group and a halogen atom or (iii) a halogen atom;

$R^2$ and $R^3$ independently represent a hydrogen atom or a $C_{1-6}$ alkyl group which may have one to four substituents selected from the group consisting of a hydroxyl group, an amino group, a carboxyl group, a nitro group, a mono- or di-$C_{1-6}$ alkylamino group, a alkoxy group, a $C_{1-6}$ alkyl-carbonyloxy group and a halogen atom;

X represents an oxygen atom, a sulfur atom or a methylene group;

Y represents (a) a group shown by the formula:

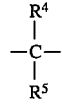

wherein $R^4$ and $R^5$ independently represent a hydrogen atom or a $C_{1-6}$ alkyl group which may have one to four substituents selected from the group consisting of a hydroxyl group, an amino group, a carboxyl group, a nitro group, a mono- or di-$C_{1-6}$ alkylamino group, a $C_{1-6}$ alkoxy group, a $C_{1-6}$ alkyl-carbonyloxy group and a halogen atom, or (b) divalent group selected from the group consisting of the formula:

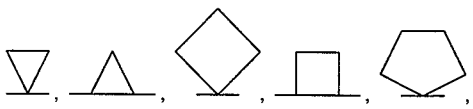

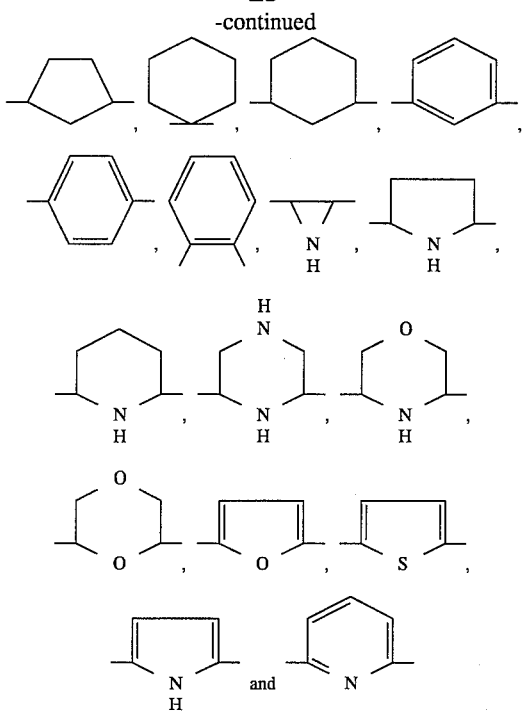

which may be substituted with one to five substituents selected from the group consisting of (i) a $C_{1-6}$ alkyl group which may be substituted with one to four substituents selected from the group consisting of a hydroxyl group, an amino group, a mono- or di-$C_{1-6}$ alkylamino group, a $C_{1-6}$ alkoxy group, a $C_{1-6}$ alkyl-carbonyloxy group and a halogen atom, (ii) an amino group which may be substituted with one to two substituents selected from a $C_{1-6}$ alkyl group and a $C_{1-6}$ acyl group, or a pyrrolidino, a morpholine, a piperidino or a 1-piperazinyl group, (iii) a hydroxyl group, (iv) a carboxyl group, (v) a nitro group, (vi) a $C_{1-6}$ alkoxy group and (vii) a halogen atom; m denotes an integer of 0 to 4; and n denotes an integer of 0 to 4, or a pharmaceutically acceptable salt thereof.

12. An antiasthmatic composition or a composition for inhibiting platelet activating factor which comprises an effective amount of a compound of the formula:

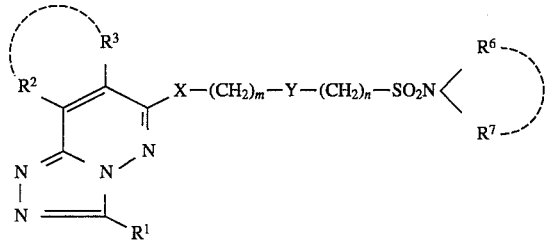

wherein all symbols are of the same meanings as defined in claim 1, or a pharmaceutically acceptable salt thereof, and a pharmaceutically acceptable carrier.

13. A method for inhibiting bronchoconstriction in a mammal by administering an anti-bronchoconstricting effective amount of a compound of claim 1 or its salt to a mammal in need thereof.

14. A method for inhibiting bronchoconstriction according to claim 13, wherein the bronchoconstriction results from an asthmatic episode.

15. A method for treating asthma in a mammal which comprises administering to a mammal suffering therefrom a therapeutically effective amount of a compound of the formula:

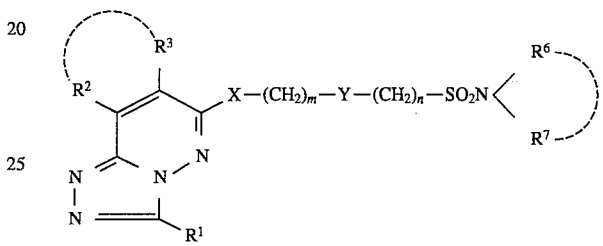

wherein all symbols are of the same meanings as defined in claim 1, or a pharmaceutically acceptable salt thereof, together with a physiologically acceptable carrier.

16. A method for treating an allergy in a mammal which comprises administering to a mammal suffering therefrom a therapeutically effective amount of a compound of the formula:

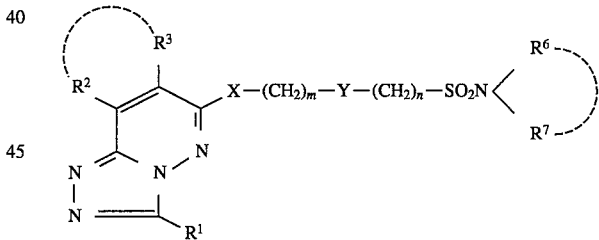

wherein all symbols are of the same meanings as defined in claim 1, or a pharmaceutically acceptable salt thereof, together with a physiologically acceptable carrier.

* * * * *